(12) United States Patent
Miyachi

(10) Patent No.: US 11,969,292 B2
(45) Date of Patent: Apr. 30, 2024

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 100 days.

(21) Appl. No.: 17/563,829

(22) Filed: Dec. 28, 2021

(65) Prior Publication Data

US 2022/0117586 A1    Apr. 21, 2022

Related U.S. Application Data

(63) Continuation of application No. PCT/JP2020/026512, filed on Jul. 7, 2020.

(30) Foreign Application Priority Data

Jul. 26, 2019  (JP) .................. 2019-137689

(51) Int. Cl.
  *A61B 8/08*    (2006.01)
  *A61B 8/00*    (2006.01)
  *A61B 8/06*    (2006.01)

(52) U.S. Cl.
  CPC .............. *A61B 8/5207* (2013.01); *A61B 8/06* (2013.01); *A61B 8/4472* (2013.01);
  (Continued)

(58) Field of Classification Search
  CPC ....... A61B 8/06; A61B 8/4472; A61B 8/4494; A61B 8/461; A61B 8/463; A61B 8/488;
  (Continued)

(56) References Cited

U.S. PATENT DOCUMENTS 6,312,385 B1    11/2001  Mo et al.
2003/0139664 A1*  7/2003  Hunt ................... G01S 7/52023
                                              600/407

(Continued)

FOREIGN PATENT DOCUMENTS

JP    2002-052026 A    2/2002
JP    2012-245021 A    12/2012
JP       6243126 B2    12/2017

OTHER PUBLICATIONS

International Search Report issued in PCT/JP2020/026512, dated Sep. 8, 2020.

(Continued)

*Primary Examiner* — Joseph M Santos Rodriguez
*Assistant Examiner* — Brooke Lyn Klein
(74) *Attorney, Agent, or Firm* — Studebaker & Brackett PC

(57) ABSTRACT

An ultrasound diagnostic apparatus (1) includes an ultrasound probe (2) and a diagnostic apparatus main body (3) that are wirelessly connected, the ultrasound probe (2) includes a detection unit (16) that generates complex baseband signals, an averaging unit (17) that averages the complex baseband signals at a plurality of sampling points in a Doppler gate set on a B-mode image to acquire average complex baseband signals, and a probe-side wireless communication circuit (20) that wirelessly transmits the average complex baseband signals, and the diagnostic apparatus main body (3) includes a main body-side wireless communication circuit (31) that receives the average complex baseband signals, and a Doppler image generation unit (33) that performs a frequency analysis on the average complex baseband signals to generate a Doppler image, and displays the Doppler image on a monitor (36).

11 Claims, 7 Drawing Sheets

(52) U.S. Cl.
CPC ............ *A61B 8/4494* (2013.01); *A61B 8/461* (2013.01); *A61B 8/488* (2013.01); *A61B 8/54* (2013.01); *A61B 8/565* (2013.01)

(58) Field of Classification Search
CPC ....... A61B 8/5207; A61B 8/5246; A61B 8/54; A61B 8/56; A61B 8/565; G01S 15/8915; G01S 15/8979; G01S 7/52034; G01S 7/5208
See application file for complete search history.

(56) References Cited

U.S. PATENT DOCUMENTS

| | | | | |
|---|---|---|---|---|
| 2007/0239001 | A1* | 10/2007 | Mehi | G01S 7/52095 600/437 |
| 2012/0010508 | A1* | 1/2012 | Sokulin | A61B 8/461 600/443 |
| 2013/0150717 | A1* | 6/2013 | Sato | A61B 8/466 600/443 |
| 2013/0226001 | A1 | 8/2013 | Steen et al. | |
| 2016/0066893 | A1* | 3/2016 | Cho | G01S 7/52084 600/459 |
| 2016/0331353 | A1* | 11/2016 | Ralston | A61B 8/546 |
| 2017/0086798 | A1* | 3/2017 | Bjaerum | A61B 8/565 |
| 2018/0028153 | A1* | 2/2018 | Kuroiwa | A61B 8/14 |
| 2019/0064349 | A1* | 2/2019 | Suzuki | A61B 5/0095 |

OTHER PUBLICATIONS

International Preliminary Report on Patentability and Written Opinion issued in PCT/JP2020/026512, dated Feb. 1, 2022.

\* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2020/026512 filed on Jul. 7, 2020, which claims priority under 35 U.S.C. § 119(a) to Japanese Patent Application No. 2019-137689 filed on Jul. 26, 2019. The above application is hereby expressly incorporated by reference, in its entirety, into the present application.

BACKGROUND OF THE INVENTION

1. Field of the Invention

The present invention relates to an ultrasound diagnostic apparatus in which an ultrasound probe and a diagnostic apparatus main body are wirelessly connected, and a control method of the ultrasound diagnostic apparatus.

2. Description of the Related Art

In the related art, in the medical field, an ultrasound diagnostic apparatus using an ultrasound image has been put to practical use. Generally, this type of ultrasound diagnostic apparatus has an ultrasound probe with a built-in transducer array, and an apparatus body connected to the ultrasound probe, transmits ultrasonic waves toward a subject from the ultrasound probe, receives ultrasound echo from the subject by the ultrasound probe, and electrically processes the reception signals by the apparatus body to generate an ultrasound image.

For example, JP2002-52026A has disclosed an ultrasound diagnostic apparatus in which a Doppler gate is installed on a B-mode image, a complex baseband signal in the Doppler gate is acquired, and a so-called Doppler image is generated on the basis of the acquired complex baseband signal.

In recent years, for example, as disclosed in JP6243126B, an ultrasound diagnostic apparatus in which an ultrasound probe and a diagnostic apparatus main body are connected to each other by wireless communication has been developed. The ultrasound probe in JP6243126B generates a complex baseband signal on the basis of a reception signal corresponding to an ultrasound echo from a subject, and wirelessly transmits the generated complex baseband signal to the diagnostic apparatus main body.

SUMMARY OF THE INVENTION

However, for example, in a case where the Doppler image as disclosed in JP2002-52026A is generated by using the ultrasound diagnostic apparatus in which the ultrasound probe and the diagnostic apparatus main body are connected to each other by wireless communication as disclosed in JP6243126B, in order to sufficiently ensure the accuracy of the generated Doppler image, it is necessary to wirelessly transmit the complex baseband signal from the ultrasound probe to the diagnostic apparatus main body while holding the complex baseband signal generated by the ultrasound probe with a large information amount. Therefore, it takes a lot of time to wirelessly transmit the complex baseband signal, and thus, for example, it may be difficult to display the Doppler image in real time on a monitor of the diagnostic apparatus main body.

The present invention has been made in order to solve such a problem in the related art, and an object thereof is to provide an ultrasound diagnostic apparatus and a control method of the ultrasound diagnostic apparatus which can reduce an information amount of data wirelessly transmitted from the ultrasound probe to the diagnostic apparatus main body.

In order to achieve the object, an ultrasound diagnostic apparatus according to an aspect of the present invention is an ultrasound diagnostic apparatus comprising an ultrasound probe including a transducer array and a diagnostic apparatus main body including a monitor that are wirelessly connected; and a pulsed wave Doppler mode, in which the ultrasound probe includes a transmission and reception circuit that causes the transducer array to transmit an ultrasonic pulse toward a subject, and performs reception focusing processing on a reception signal output from the transducer array that has received an ultrasound echo from the subject to generate a sound ray signal, a detection unit that generates complex baseband signals on the basis of the sound ray signal generated by the transmission and reception circuit, an averaging unit that averages the complex baseband signals at a plurality of sampling points in a Doppler gate set on a B-mode image to acquire average complex baseband signals, and a probe-side wireless communication circuit that wirelessly transmits the average complex baseband signals acquired by the averaging unit, and the diagnostic apparatus main body includes a main body-side wireless communication circuit that receives the average complex baseband signals wirelessly transmitted from the probe-side wireless communication circuit, and a Doppler image generation unit that performs a frequency analysis on the average complex baseband signals received by the main body-side wireless communication circuit to generate a Doppler image, and displays the Doppler image on the monitor.

It is preferable that the number of the plurality of sampling points has a lower limit value decided according to a wirelessly transmittable data amount per unit time based on a wireless connection status between the probe-side wireless communication circuit and the main body-side wireless communication circuit.

In this case, it is preferable that the ultrasound probe includes a sampling point setting unit that sets the number of the plurality of sampling points in the Doppler gate such that a wireless transmission data amount per unit time required for wirelessly transmitting the complex baseband signals at the plurality of sampling points without averaging exceeds the wirelessly transmittable data amount and a wireless transmission data amount per unit time required for wirelessly transmitting the average complex baseband signals is equal to or less than the wirelessly transmittable data amount.

The ultrasound probe may include a high-pass filter that performs high-pass processing on the average complex baseband signals acquired by the averaging unit, and the probe-side wireless communication circuit may wirelessly transmit the average complex baseband signals that are subjected to the high-pass processing by the high-pass filter.

The diagnostic apparatus main body may include a high-pass filter that performs high-pass processing on the average complex baseband signals received by the main body-side wireless communication circuit, and the Doppler image generation unit may perform the frequency analysis on the average complex baseband signals that are subjected to the high-pass processing by the high-pass filter.

In this case, the diagnostic apparatus main body may include a speaker connected to an output side of the high-pass filter.

It is preferable that the Doppler image generation unit includes a fast Fourier transformer.

Further, the ultrasound probe may include a time stamping unit that assigns a time stamp to the average complex baseband signals.

In this case, the diagnostic apparatus main body may include an unreceivable sample number detection unit that detects the number of samples of the average complex baseband signals that could not be received by the main body-side wireless communication circuit, on the basis of the time stamp assigned to the average complex baseband signals.

Further, in a case where the number of samples detected by the unreceivable sample number detection unit is equal to or less than a predetermined threshold value, the Doppler image generation unit may perform interpolation processing on the average complex baseband signals, and generate the Doppler image on the basis of the interpolated average complex baseband signals.

The Doppler image generation unit may stop the generation of the Doppler image in a case where the number of samples detected by the unreceivable sample number detection unit exceeds a threshold value.

The ultrasound probe may include a memory that saves the average complex baseband signals acquired by the averaging unit, the probe-side wireless communication circuit may wirelessly transmit the average complex baseband signals saved in the memory to the diagnostic apparatus main body in a case where the display of the Doppler image on the monitor by the Doppler image generation unit is frozen, and the Doppler image generation unit may perform the frequency analysis on the average complex baseband signals that have been saved in the memory, instead of the lost average complex baseband signals, on the basis of the time stamp assigned to the average complex baseband signals, to generate again the Doppler image, and display the Doppler image on the monitor.

A control method of an ultrasound diagnostic apparatus according to another aspect of the present invention is a control method of an ultrasound diagnostic apparatus that includes an ultrasound probe including a transducer array and a diagnostic apparatus main body including a monitor that are wirelessly connected; and a pulsed wave Doppler mode, and the control method comprises, in the ultrasound probe, causing the transducer array to transmit an ultrasonic pulse toward a subject, and performing reception focusing processing on a reception signal output from the transducer array that has received an ultrasound echo from the subject to generate a sound ray signal, generating complex baseband signals on the basis of the generated sound ray signal, averaging the complex baseband signals at a plurality of sampling points in a Doppler gate set on a B-mode image to acquire average complex baseband signals, and wirelessly transmitting the acquired average complex baseband signals, and in the diagnostic apparatus main body, receiving the average complex baseband signals wirelessly transmitted from the ultrasound probe, and performing a frequency analysis on the received average complex baseband signals to generate a Doppler image, and displaying the Doppler image on the monitor.

According to the present invention, the ultrasound probe includes the detection unit that generates complex baseband signals on the basis of the sound ray signal generated by the transmission and reception circuit, the averaging unit that averages the complex baseband signals at the plurality of sampling points in the Doppler gate set on the B-mode image to acquire average complex baseband signals, and the probe-side wireless communication circuit that wirelessly transmits the average complex baseband signals acquired by the averaging unit, and the diagnostic apparatus main body includes the main body-side wireless communication circuit that receives the average complex baseband signals wirelessly transmitted from the probe-side wireless communication circuit, and the Doppler image generation unit that performs the frequency analysis on the average complex baseband signals received by the main body-side wireless communication circuit to generate the Doppler image, and displays the Doppler image on the monitor. Therefore, it is possible to reduce the information amount of the data wirelessly transmitted from the ultrasound probe to the diagnostic apparatus main body.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
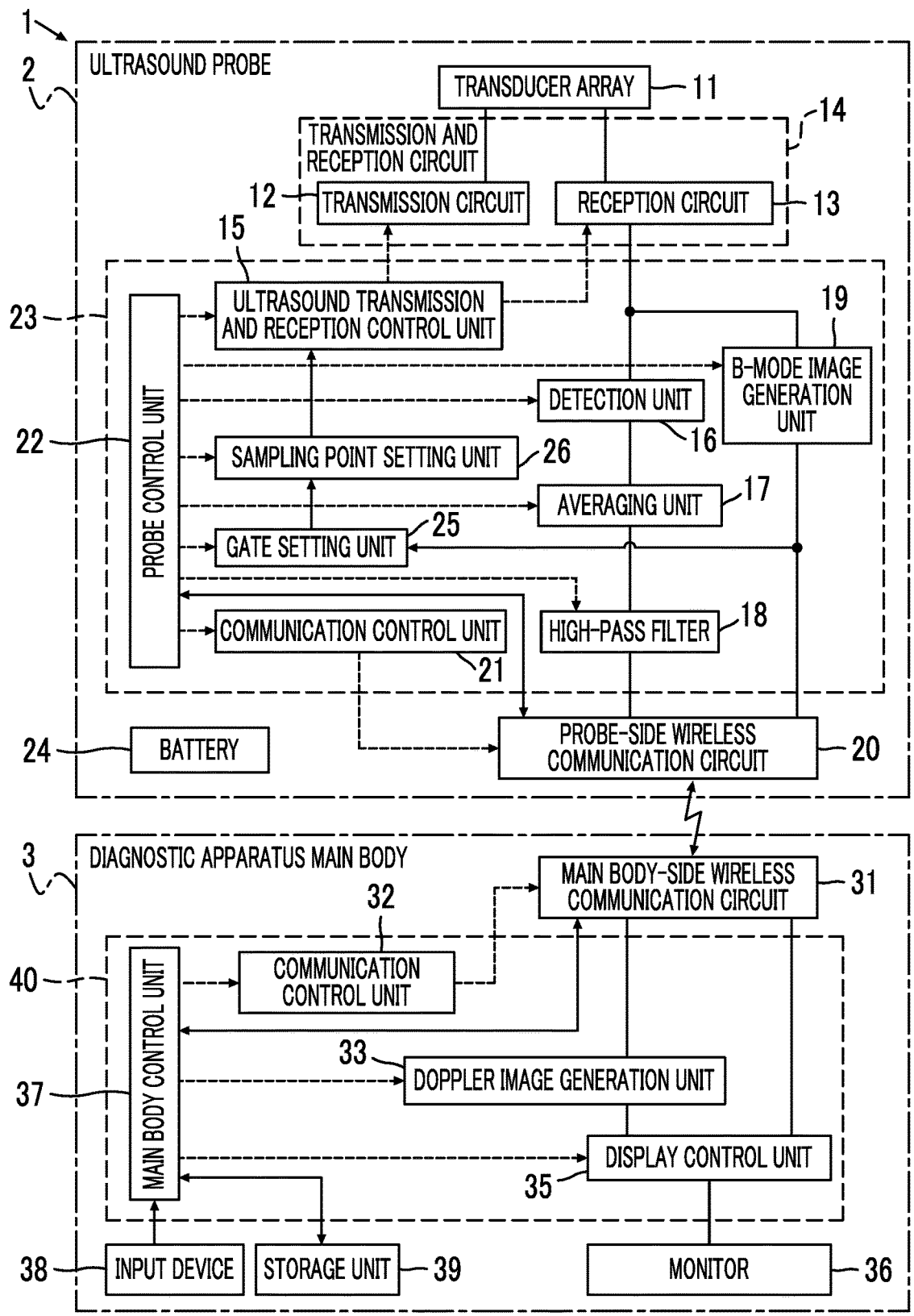
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. The ultrasound diagnostic apparatus 1 is an ultrasound diagnostic apparatus that has an ultrasound probe 2, and a diagnostic apparatus main body 3 wirelessly connected to the ultrasound probe 2, and comprises a pulsed wave Doppler mode. Here, the "pulsed wave Doppler mode" refers to a mode in which a graph indicating a relationship between a blood flow velocity in a blood vessel of a subject and a measurement time, is displayed in real time.

As illustrated in FIG. 1, the ultrasound probe 2 has a transducer array 11, and a transmission circuit 12 and a reception circuit 13 are connected to the transducer array 11. Here, the transmission circuit 12 and the reception circuit 13 constitute a transmission and reception circuit 14. An ultrasound transmission and reception control unit 15 is connected to the transmission circuit 12 and the reception circuit 13. Further, a detection unit 16, an averaging unit 17, and a high-pass filter 18 are sequentially connected to the reception circuit 13. A B-mode image generation unit 19 is connected to the reception circuit 13. Further, a probe-side wireless communication circuit 20 is connected to the high-pass filter 18 and the B-mode image generation unit 19. A gate setting unit 25 is connected to the B-mode image generation unit 19, and a sampling point setting unit 26 is connected to the gate setting unit 25. The ultrasound transmission and reception control unit 15 is connected to the sampling point setting unit 26. Further, a communication control unit 21 is connected to the probe-side wireless communication circuit 20. The probe-side wireless communication circuit 20 and a probe control unit 22 are connected so as to exchange information bidirectionally.

The probe control unit 22 is connected to the ultrasound transmission and reception control unit 15, the detection unit 16, the averaging unit 17, the high-pass filter 18, the B-mode image generation unit 19, the communication control unit 21, the gate setting unit 25, and the sampling point setting unit 26. Further, the ultrasound transmission and reception control unit 15, the detection unit 16, the averaging unit 17, the high-pass filter 18, the B-mode image generation unit 19, the communication control unit 21, the probe control unit 22, the gate setting unit 25, and the sampling point setting unit 26 constitute a probe-side processor 23. The ultrasound probe 2 has a battery 24.

The diagnostic apparatus main body 3 has a main body-side wireless communication circuit 31 that is wirelessly connected to the probe-side wireless communication circuit 20 of the ultrasound probe 2, and a communication control unit 32 is connected to the main body-side wireless communication circuit 31. A Doppler image generation unit 33 and a display control unit 35 are sequentially connected to the main body-side wireless communication circuit 31. The display control unit 35 is directly connected to the main body-side wireless communication circuit 31. A monitor 36 is connected to the display control unit 35.

A main body control unit 37 is connected to the communication control unit 32, the Doppler image generation unit 33, and the display control unit 35, and an input device 38 and a storage unit 39 are connected to the main body control unit 37. Here, the main body control unit 37 and the storage unit 39 are connected so as to exchange information bidirectionally. Further, the communication control unit 32, the Doppler image generation unit 33, the display control unit 35, and the main body control unit 37 constitute a main body-side processor 40.

The transducer array 11 of the ultrasound probe 2 illustrated in FIG. 1 has a plurality of transducers arranged in a one-dimensional or two-dimensional manner. According to a drive signal supplied from the transmission circuit 12, each of the transducers transmits an ultrasonic wave and receives an ultrasound echo from a subject to output a signal based on the ultrasound echo. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The ultrasound transmission and reception control unit 15 controls the transmission circuit 12 and the reception circuit 13 to cause the transducer array 11 to perform transmission of ultrasound beams and reception of ultrasound echoes on the basis of an inspection mode and a scanning method instructed from the probe control unit 22. Here, the inspection mode includes at least a brightness mode (B mode) and a pulsed wave Doppler mode (PW mode), and also includes inspection modes such as a color flow mode (CF mode) and a continuous wave Doppler mode (CW mode) that can be used in the ultrasound diagnostic apparatus, and the scanning method indicates, for example, any one of an electronic sector scanning method, an electronic linear scanning method, an electronic convex scanning method, or the like.

The transmission circuit 12 includes, for example, a plurality of pulse generators, and the transmission circuit 12 adjusts the amount of delay of each drive signal so that ultrasonic waves transmitted from the plurality of transducers of the transducer array 11 form an ultrasound beam on the basis of a transmission delay pattern selected according to a control signal from the ultrasound transmission and reception control unit 15, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11 of the ultrasound probe 2. The ultrasound echo propagating toward the transducer array 11 in this manner is received by each transducer constituting the transducer array 11. In this case, each transducer constituting the transducer array 11 expands and contracts by receiving the propagating ultrasound echo to generate an electric signal, and outputs the electric signal to the reception circuit 13.

Figure 2:
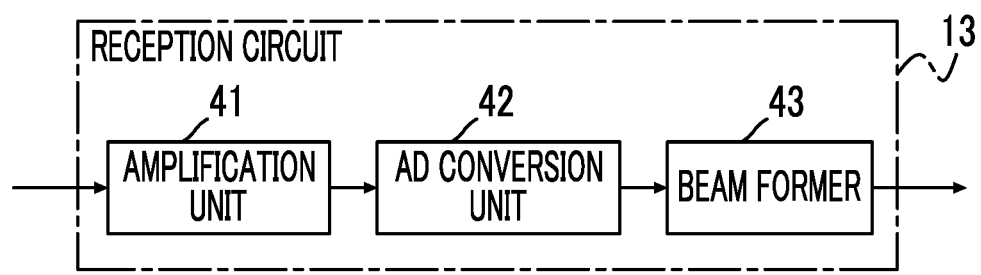
FIG. 2 is a block diagram illustrating an internal configuration of a reception circuit in the first embodiment of the present invention.

The reception circuit 13 processes the signal output from the transducer array 11 according to the control signal from the ultrasound transmission and reception control unit 15 to generate a sound ray signal. As illustrated in FIG. 2, the reception circuit 13 has a configuration in which an amplification unit 41, an analog digital (AD) conversion unit 42, and a beam former 43 are connected in series.

The amplification unit 41 amplifies the signals input from each transducer constituting the transducer array 11, and transmits the amplified signals to the AD conversion unit 42. The AD conversion unit 42 converts the signal transmitted from the amplification unit 41 into digital reception data, and transmits the reception data to the beam former 43. The beam former 43 performs so-called reception focusing processing in which addition is performed by giving delays to respective pieces of the reception data converted by the AD conversion unit 42 according to a sound velocity distribution or a sound velocity set on the basis of a reception delay pattern selected according to the control signal from the ultrasound transmission and reception control unit 15. Through the reception focusing processing, a sound ray signal in which each piece of the reception data converted by the AD conversion unit 42 is phased and added and the focus of the ultrasound echo is narrowed is acquired.

Figure 3:
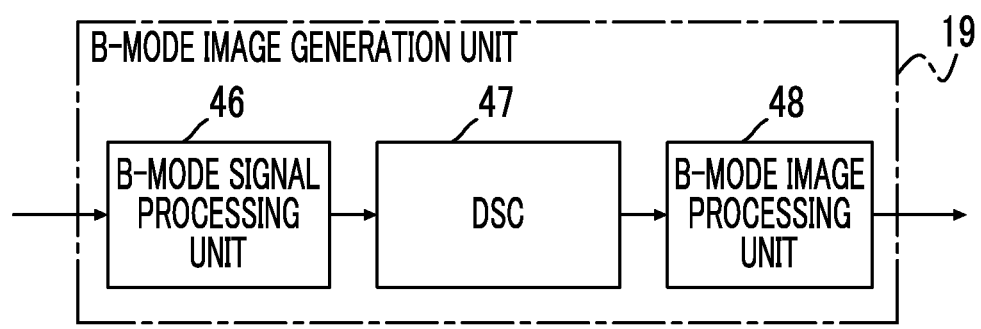
FIG. 3 is a block diagram illustrating an internal configuration of a B-mode image generation unit in the first embodiment of the present invention.

The B-mode image generation unit 19 generates a so-called B-mode image on the basis of the sound ray signal generated by the beam former 43 of the reception circuit 13. As illustrated in FIG. 3, the B-mode image generation unit 19 has a configuration in which a B-mode signal processing unit 46, a digital scan converter (DSC) 47, and a B-mode image processing unit 48 are sequentially connected in series.

The B-mode signal processing unit 46 generates a B-mode image signal, which is tomographic image information regarding the body tissues of the subject, by performing, on the sound ray signal generated by the reception circuit 13, correction of the attenuation due to the distance according to the depth of the reflection position of the ultrasonic wave and then performing envelope detection processing.

The DSC 47 converts (raster conversion) the B-mode image signal generated by the B-mode signal processing unit 46 into an image signal according to a normal television signal scanning method.

The B-mode image processing unit 48 performs various kinds of necessary image processing such as gradation processing on the B-mode image signal input from the DSC 47.

The B-mode image signal processed in such a manner is simply referred to as a B-mode image.

Figure 4:
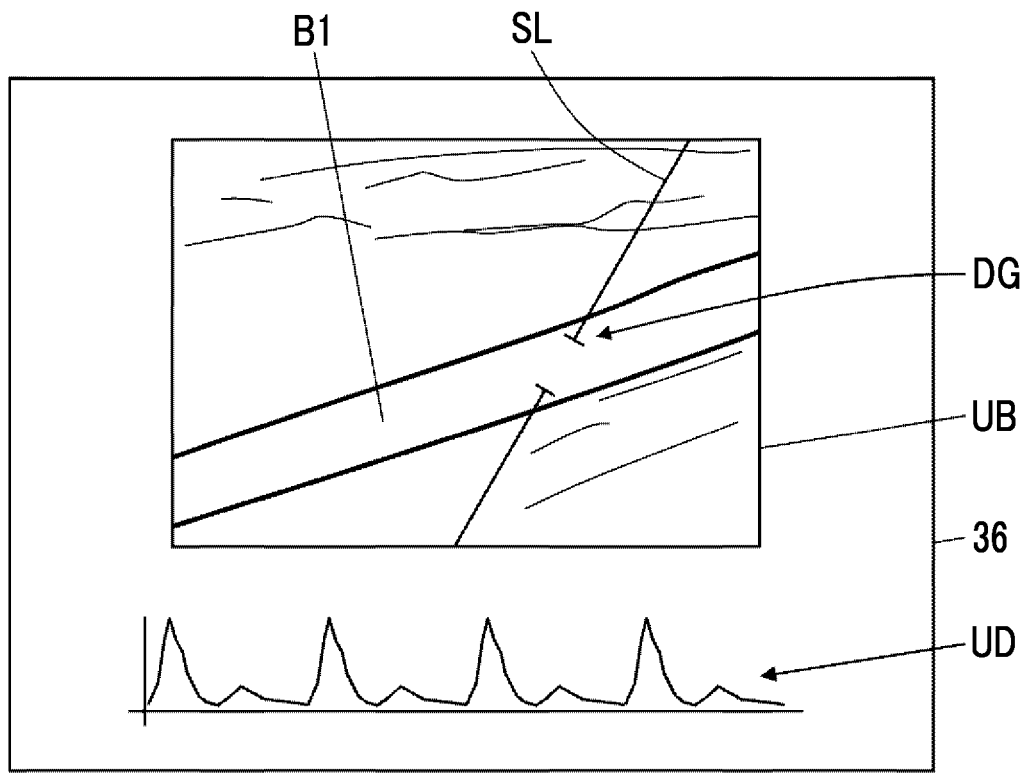
FIG. 4 is a diagram schematically illustrating a B-mode image and a Doppler image in the first embodiment of the present invention.

As illustrated in FIG. 4, the gate setting unit 25 sets a so-called Doppler gate DG in a blood vessel region B1 on a B-mode image UB generated by the B-mode image generation unit 19. In the example illustrated in FIG. 4, a straight line portion SL extends from the Doppler gate DG, but the straight line portion SL corresponds to a scan line of the ultrasound beam in the pulsed wave Doppler mode, which passes through the center of the Doppler gate DG. Further, the gate setting unit 25 can set the Doppler gate DG on the B-mode image UB according to instruction information input by an operator through the input device 38 of the diagnostic apparatus main body 3, for example. In this case, the instruction information input by the operator through the input device 38 can be input to the gate setting unit 25 via the main body control unit 37, the main body-side wireless communication circuit 31, the probe-side wireless communication circuit 20, and the probe control unit 22, for example.

Figure 5:
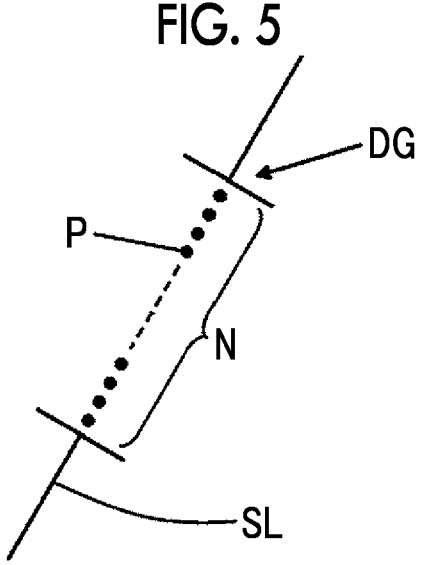
FIG. 5 is a diagram schematically illustrating a Doppler gate in the first embodiment of the present invention.

The sampling point setting unit 26 sets a plurality of sampling points P on an extension line of the straight line portion SL in the Doppler gate DG, as illustrated in FIG. 5. In the example illustrated in FIG. 5, N sampling points P are set. The sampling point setting unit 26 can set, for example, a predetermined number N of sampling points P in the Doppler gate DG.

The detection unit 16 generates so-called complex baseband signals I and Q, which are two types of signals of which the phases are orthogonal to each other, on the basis of the sound ray signal generated by the transmission and reception circuit 14 in the pulsed wave Doppler mode. More specifically, the detection unit 16 mixes the sound ray signal generated by the reception circuit 13 with a carrier signal having a reference frequency to perform quadrature detection on the sound ray signal, and converts the sound ray signal into the complex baseband signals I and Q.

The averaging unit 17 averages the complex baseband signals I and Q at the plurality of sampling points P in the Doppler gate DG set on the B-mode image UB by the gate setting unit 25, and acquires average complex baseband signals X and Y.

The high-pass filter 18 functions as a so-called wall filter, and removes a signal of a low frequency component derived from the motion of the body tissue of the subject, which is a so-called clutter signal, from the average complex baseband signals X and Y acquired by the averaging unit 17.

The probe-side wireless communication circuit 20 includes an antenna for transmitting and receiving radio waves, modulates a carrier on the basis of the average complex baseband signals X and Y subjected to the high-pass processing by the high-pass filter 18 and the B-mode image UB generated by the B-mode image generation unit 19, and generates a transmission signal indicating the average complex baseband signals X and Y and a transmission signal indicating the B-mode image UB. The probe-side wireless communication circuit 20 transmits radio waves from the antenna by supplying the transmission signals generated in this manner to the antenna, and sequentially and wirelessly transmits the average complex baseband signals X and Y and the B-mode image UB to the diagnostic apparatus main body 3. As the modulation method of the carrier, amplitude shift keying (ASK), phase shift keying (PSK), quadrature phase shift keying (QPSK), 16 quadrature amplitude modulation (16QAM), or the like is used.

The probe-side wireless communication circuit 20 receives a transmission signal indicating the instruction information for controlling the ultrasound probe 2, from the diagnostic apparatus main body 3, and sends the instruction information acquired by demodulating the received transmission signal, to the probe control unit 22. Here, the instruction information can be input by the operator through the input device 38 of the diagnostic apparatus main body 3, for example.

The communication control unit 21 of the ultrasound probe 2 controls the probe-side wireless communication circuit 20 such that the transmission of the average complex baseband signals X and Y and the B-mode image UB to the diagnostic apparatus main body 3 and the reception of the instruction information from the diagnostic apparatus main body 3 are performed with a transmission and reception radio field intensity set by the probe control unit 22.

The probe control unit 22 controls each unit of the ultrasound probe 2 on the basis of a program and the like stored in advance.

The battery 24 is built in the ultrasound probe 2, and supplies power to each circuit of the ultrasound probe 2.

The probe-side processor 23 having the ultrasound transmission and reception control unit 15, the detection unit 16, the averaging unit 17, the high-pass filter 18, the B-mode image generation unit 19, the communication control unit 21, the probe control unit 22, the gate setting unit 25, and the sampling point setting unit 26 is configured by a central processing unit (CPU) and a control program for causing the CPU to execute various kinds of processing, but the probe-side processor 23 may be configured by using a field programmable gate array (FPGA), a digital signal processor (DSP), an application specific integrated circuit (ASIC), a graphics processing unit (GPU), or other integrated circuits (IC) or may be configured by a combination thereof.

The ultrasound transmission and reception control unit 15, the detection unit 16, the averaging unit 17, the high-pass filter 18, the B-mode image generation unit 19, the communication control unit 21, the probe control unit 22, the gate setting unit 25, and the sampling point setting unit 26 of the probe-side processor 23 can also be configured by being integrated partially or entirely into one CPU or the like.

The main body-side wireless communication circuit 31 of the diagnostic apparatus main body 3 includes an antenna for transmitting and receiving radio waves, receives the transmission signal indicating the average complex baseband signals X and Y and the transmission signal indicating the B-mode image UB which are transmitted from the probe-side wireless communication circuit 20 of the ultrasound probe 2 via the antenna, and demodulates the received transmission signals to output the average complex baseband signals X and Y and the B-mode image UB. Further, the main body-side wireless communication circuit 31 sends the output average complex baseband signals X and Y to the Doppler image generation unit 33, and sends the B-mode image UB to the display control unit 35. The main body-side wireless communication circuit 31 receives the instruction information input by the operator through the input device 38, via the main body control unit 37, generates a transmission signal indicating the instruction information, and transmits the generated transmission signal to the ultrasound probe 2.

The Doppler image generation unit 33 performs a frequency analysis on the average complex baseband signals X and Y sent from the main body-side wireless communication circuit 31 to generate a Doppler image UD as illustrated in FIG. 4. Although not illustrated, more specifically, the Doppler image generation unit 33 has a fast Fourier transformer that performs the frequency analysis by performing a Fourier transform on the average complex baseband signals X and Y to generate spectrum signals, and the Doppler image generation unit 33 generates a Doppler image signal by aligning the spectrum signals generated by the fast Fourier transformer on a time axis and expressing the magnitude of each frequency component in brightness. The Doppler image signal generated in such a manner is simply referred to as a Doppler image. As illustrated in FIG. 4, in the Doppler image UD, the lateral axis indicates a time axis, the vertical axis indicates a Doppler shift frequency, that is, a flow velocity, and the brightness of the waveform represents power in each frequency component.

The display control unit 35 performs predetermined processing on the Doppler image UD generated by the Doppler image generation unit 33 and the B-mode image UB sent from the main body-side wireless communication circuit 31 to display the Doppler image UD and the B-mode image UB on the monitor 36 under the control of the main body control unit 37.

The monitor 36 is for displaying the Doppler image UD, the B-mode image UB, and the like under the control of the display control unit 35, and includes a display device such as a liquid crystal display (LCD), or an organic electroluminescence (EL) display.

The communication control unit 32 of the diagnostic apparatus main body 3 controls the main body-side wireless communication circuit 31 such that the reception of the transmission signal transmitted from the probe-side wireless communication circuit 20 of the ultrasound probe 2 and the transmission of the instruction information input from the operator through the input device 38 are performed.

The main body control unit 37 controls each unit of the diagnostic apparatus main body 3 on the basis of a program stored in advance in the storage unit 39 or the like and the operator's input operation through the input device 38.

The input device 38 is for the operator to perform an input operation, and can be configured to comprise a keyboard, a mouse, a trackball, a touchpad, a touch panel, and the like.

The storage unit 39 stores a control program and the like of the diagnostic apparatus main body 3, and recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The main body-side processor 40 having the communication control unit 32, the Doppler image generation unit 33, the display control unit 35, and the main body control unit 37 is configured by a CPU and a control program causing the CPU to execute various kinds of processing, but may be configured by using FPGA, DSP, ASIC, GPU, or other ICs, or may be configured by a combination thereof.

In addition, the communication control unit 32, the Doppler image generation unit 33, the display control unit 35, and the main body control unit 37 of the main body-side processor 40 can also be configured by being integrated partially or entirely into one CPU or the like.

Figure 6:
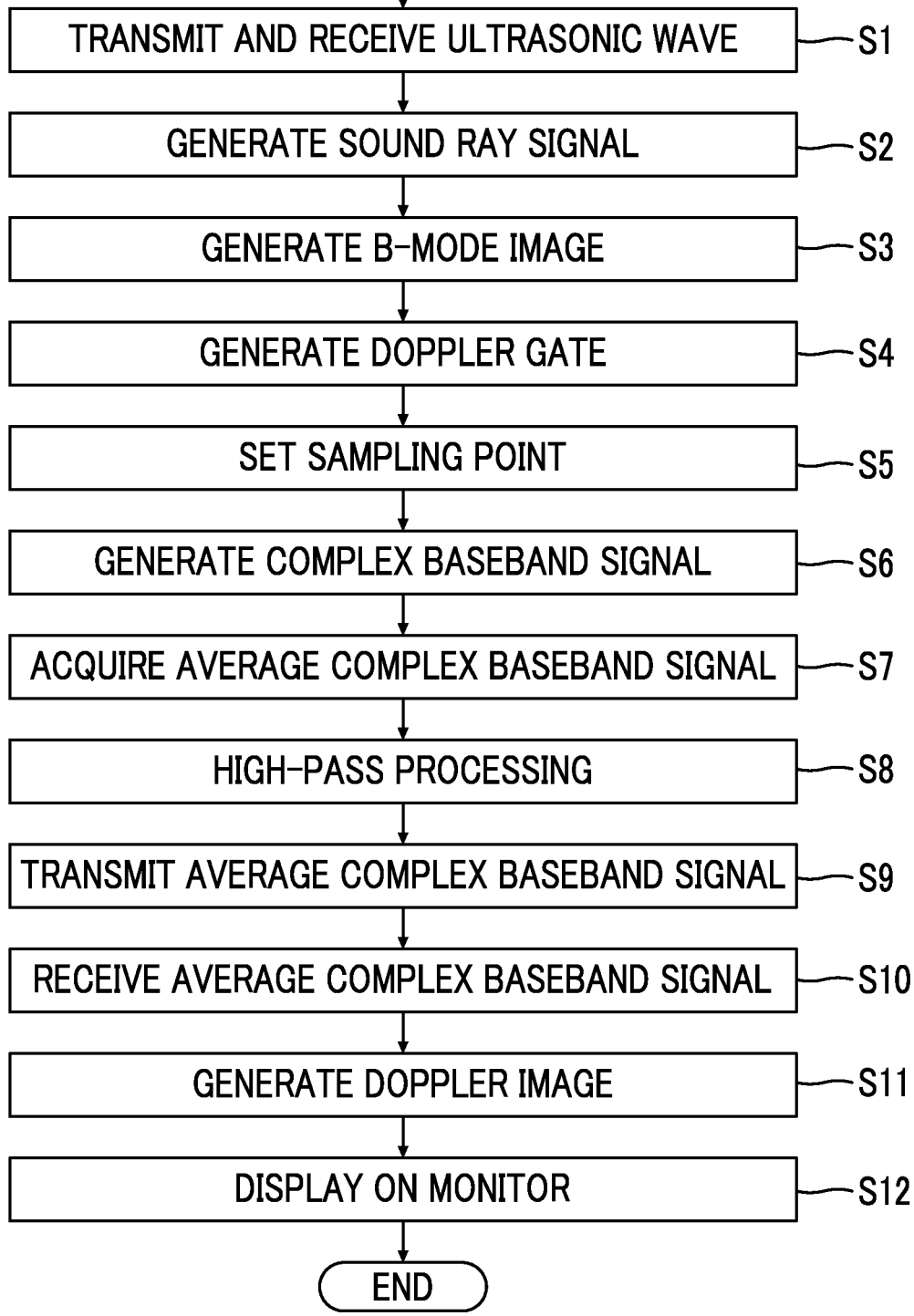
FIG. 6 is a flowchart illustrating an operation of the ultrasound diagnostic apparatus according to the first embodiment of the present invention.

Next, the operation of the ultrasound diagnostic apparatus 1 according to the first embodiment, from the transmission of the ultrasonic waves into the subject to displaying the Doppler image UD on the monitor 36 will be described with reference to the flowchart of FIG. 6.

First, the ultrasound probe 2 is brought into contact with a body surface of the subject by the operator, and the ultrasound beam is transmitted into the subject from the plurality of transducers of the transducer array 11 according to the drive signal of the transmission circuit 12 under the control of the ultrasound transmission and reception control unit 15. The ultrasound echo based on the transmitted ultrasound beam is received by each transducer, the reception signal as the analog signal is output to the reception circuit 13, is amplified in the amplification unit 41, and is subjected to the AD conversion in the AD conversion unit 42, and thereby the reception data is acquired (Step S1). By performing the reception focusing processing on the reception data by the beam former 43, a sound ray signal is generated (Step S2). Here, the transmission circuit 12 transmits the drive signal to each transducer of the transducer array 11 such that the transmissions of the ultrasonic waves according to the B mode and the pulsed wave Doppler mode are sequentially and alternately performed, under the control of the ultrasound transmission and reception control unit 15.

The sound ray signal generated on the basis of the ultrasonic waves transmitted from the transducer array 11 into the subject according to the B mode is input to the B-mode image generation unit 19, and is converted into the B-mode image UB including at least the blood vessel region B1 by the B-mode image generation unit 19 (Step S3). In this case, the B-mode signal processing unit 46 performs the correction of the attenuation due to the distance according to the depth of the reflection position of the ultrasonic wave and the envelope detection processing, the DSC 47 performs the conversion into the image signal according to a normal television signal scanning method, and the B-mode image processing unit 48 performs various kinds of necessary image processing such as gradation processing.

The B-mode image UB generated by the B-mode image generation unit 19 is wirelessly transmitted from the probe-side wireless communication circuit 20 to the diagnostic apparatus main body 3 under the control of the communication control unit 21. The B-mode image UB wirelessly transmitted from the probe-side wireless communication circuit 20 to the diagnostic apparatus main body 3 is received by the main body-side wireless communication circuit 31, is sent to the display control unit 35, and is displayed on the monitor 36 as illustrated in FIG. 4, for example.

In a case where the B-mode image UB is generated and displayed on the monitor 36 in this manner, for example, when the operator inputs the instruction information through the input device 38, the gate setting unit 25 sets the Doppler gate DG in the blood vessel region B1 on the B-mode image UB, for example, as illustrated in FIG. 4, according to the input instruction information (Step S4). In the example illustrated in FIG. 4, the straight line portion SL extends from the Doppler gate DG, but the straight line portion SL corresponds to the scan line of the ultrasound beam in the pulsed wave Doppler mode, which passes through the center of the Doppler gate DG.

Next, the sampling point setting unit 26 sets a plurality of (N) sampling points P on the extension line of the straight line portion SL in the Doppler gate DG set by the gate setting unit 25, as illustrated in FIG. 5, for example (Step S5). The sampling point setting unit 26 can set, for example, the predetermined number N of sampling points P in the Doppler gate DG.

The sound ray signal generated on the basis of the ultrasonic waves transmitted from the transducer array 11 into the subject according to the pulsed wave Doppler mode is input to the detection unit 16. The detection unit 16 mixes the sound ray signal generated by the reception circuit 13 with a carrier signal having a reference frequency to perform quadrature detection on the sound ray signal, and converts the sound ray signal into complex baseband signals I and Q (Step S6).

The averaging unit 17 averages the complex baseband signals I and Q at the plurality of sampling points P in the Doppler gate DG set on the B-mode image UB by the gate setting unit 25 to acquire the average complex baseband signals X and Y (Step S7).

Here, normally, in order to sufficiently ensure the accuracy of the generated Doppler image UD, it is known that it is necessary to quantize and hold the complex baseband signals I and Q held with a large information amount of 15 bits or more each, that is, 30 bits in total. Further, in the pulsed wave Doppler mode, the repetition frequency of the ultrasonic pulse and the number N of sampling points P set in the Doppler gate DG are typically about 20 kHz and 32, respectively. Therefore, in a case where it is assumed that averaging is not performed by the averaging unit 17, the transfer speed of the complex baseband signals I and Q required for the Doppler images UD, which are to be generated, to be displayed in real time on the monitor 36 is (number N of sampling points P)×(information amount of each of complex baseband signals I and Q)×2×(repetition frequency of ultrasonic pulse)=32×15 bit×2×20 kHz=20.5 Mbps.

In the present invention, since the complex baseband signals I and Q at N sampling points P are averaged so that the average complex baseband signals X and Y are generated by the averaging unit 17, even in a case where the number N of sampling points P is 32, the information amount per type of the average complex baseband signals X and Y is 15 bits, and the repetition frequency of the ultrasonic pulse is 20 kHz, the transfer speed of the average complex baseband signals X and Y required for the Doppler images UD, which are to be generated, to be displayed in real time on the monitor 36 is 32×15 bit×2×20 kHz/32=0.6 Mbps, and thus it can be seen that the information amount of the data wirelessly transmitted is significantly reduced as compared with the case where the complex baseband signals I and Q are not averaged. Thereby, for example, it is possible to significantly reduce the time required for wirelessly transmitting the average complex baseband signals X and Y from the ultrasound probe 2 to the diagnostic apparatus main body 3.

Next, the high-pass filter 18 removes a signal of a low frequency component derived from the motion of the body tissue of the subject, which is a so-called clutter signal, from the average complex baseband signals X and Y acquired by the averaging unit 17 (Step S8).

The probe-side wireless communication circuit 20 wirelessly transmits the average complex baseband signals X and Y subjected to the high-pass processing by the high-pass filter 18, to the diagnostic apparatus main body 3 under the control of the communication control unit 21 of the ultrasound probe 2 (Step S9).

The main body-side wireless communication circuit 31 of the diagnostic apparatus main body 3 receives the average complex baseband signals X and Y that are wirelessly transmitted from the ultrasound probe 2, under the control of the communication control unit 32 of the diagnostic apparatus main body 3 (Step S10). Further, the main body-side wireless communication circuit 31 sends the received average complex baseband signals X and Y to the Doppler image generation unit 33.

The Doppler image generation unit 33 performs the frequency analysis by performing a Fourier transform on the average complex baseband signals X and Y, which are sent from the main body-side wireless communication circuit 31, to generate spectrum signals, and the Doppler image generation unit 33 generates the Doppler image UD as illustrated in FIG. 4 by aligning the generated spectrum signals on a time axis and expressing the magnitude of each frequency component in brightness (Step S11).

The generated Doppler image UD is sent to the display control unit 35, is subjected to predetermined processing, and then is displayed on the monitor 36 as illustrated in FIG. 4 (Step S12).

From the above, with the ultrasound diagnostic apparatus 1 according to the first embodiment of the present invention, the complex baseband signals I and Q are generated by the detection unit 16 on the basis of the sound ray signal generated by the transmission and reception circuit 14, the complex baseband signals I and Q at the plurality of sampling points P in the Doppler gate DG set on the B-mode image UB are averaged so that the average complex baseband signals X and Y are acquired by the averaging unit 17, and the average complex baseband signals X and Y are wirelessly transmitted from the ultrasound probe 2 to the diagnostic apparatus main body 3. Therefore, it is possible to significantly reduce the information amount of the data wirelessly transmitted from the ultrasound probe 2 to the diagnostic apparatus main body 3 as compared with the case where the complex baseband signals I and Q immediately after being generated by the detection unit 16 are wirelessly transmitted.

In a case where the complex baseband signals I and Q immediately after being generated by the detection unit 16 are wirelessly transmitted from the ultrasound probe 2 to the diagnostic apparatus main body 3, since it takes a lot of time to wirelessly transmit the complex baseband signals I and Q due to the large information amount of the complex baseband signals I and Q, it may difficult to display the Doppler image UD generated by the Doppler image generation unit 33 in real time on the monitor 36. However, with the ultrasound diagnostic apparatus 1 according to the first embodiment of the present invention, since the average complex baseband signals X and Y with small information amount are wirelessly transmitted from the ultrasound probe 2 to the diagnostic apparatus main body 3, it is possible to significantly reduce the time required for wirelessly transmitting the average complex baseband signals X and Y, and as a result, it is possible to display the Doppler image UD generated by the Doppler image generation unit 33 in real time on the monitor 36.

In general, the communication state of the wireless communication may become unstable due to the surrounding radio wave environment and the like. Thus, in a case where the communication state of the wireless communication is unstable, so-called data loss in which wirelessly transmitted data is not received on the receiving device side may occur. With the ultrasound diagnostic apparatus 1 according to the first embodiment of the present invention, since the complex baseband signals I and Q at the plurality of sampling points P are averaged by the averaging unit 17, the information amount of the data wirelessly transmitted is reduced as compared with the case where the complex baseband signals I and Q immediately after being generated by the detection unit 16 are wirelessly transmitted, and therefore, it is possible to suppress the occurrence of the data loss.

An example has been described in which the transmission circuit 12 transmits the drive signal to each transducer of the transducer array 11 such that the transmissions of the ultrasonic waves according to the B mode and the pulsed wave Doppler mode are sequentially and alternately performed, and the Doppler image UD and the B-mode image UB are generated in parallel, but the timing at which the Doppler image UD and the B-mode image UB are generated is not limited thereto. For example, the inspection mode is changed from the B mode to the pulsed wave Doppler mode with the freezing of the B-mode image UB as a trigger, and the generation of the Doppler image UD can be performed. Here, the freezing of the B-mode image UB refers to temporarily stopping the generation of the B-mode images UB being consecutively generated and the display on the monitor 36.

In this case, for example, the B-mode images UB are consecutively generated by the B-mode image generation unit 19, the Doppler gate DG is set on the B-mode image UB by the gate setting unit 25, the plurality of sampling points P are set in the Doppler gate DG by the sampling point setting unit 26, and the B-mode image UB is frozen. In a case where the B-mode image UB is frozen, the inspection mode is changed from the B mode to the pulsed wave Doppler mode, and the transmission and reception of the ultrasonic pulse according to the pulsed wave Doppler mode are performed. The reception signal generated by the reception circuit 13 is subjected to the quadrature detection processing by the detection unit 16 so that the complex baseband signals I and Q are generated, and the complex baseband signals I and Q at the plurality of sampling points P in the Doppler gate DG are averaged so that the average complex baseband signals X and Y are generated by the averaging unit 17. In a case where the average complex baseband signals X and Y are subjected to the high-pass processing by the high-pass filter 18, the average complex baseband signals X and Y are wirelessly transmitted from the probe-side wireless communication circuit 20 to the diagnostic apparatus main body 3, and are received by the main body-side wireless communication circuit 31 of the diagnostic apparatus main body 3. The Doppler image UD is generated by the Doppler image generation unit 33 on the basis of the average complex baseband signals X and Y received by the main body-side wireless communication circuit 31, and the generated Doppler image UD is displayed on the monitor 36 by the display control unit 35.

In the ultrasound diagnostic apparatus 1 illustrated in FIG. 1, the reception circuit 13 of the transmission and reception circuit 14 of the ultrasound probe 2 has the beam former 43 together with the amplification unit 41 and the AD conversion unit 42, but the beam former 43 may be disposed between the reception circuit 13, and the detection unit 16 and the B-mode image generation unit 19, instead of being disposed inside the reception circuit 13. In this case, the beam former 43 can constitute the probe-side processor 23.

The B-mode image generation unit 19 of the ultrasound probe 2 has the B-mode signal processing unit 46, the DSC 47, and the B-mode image processing unit 48, but among theses, the DSC 47 and the B-mode image processing unit 48 may be disposed between the main body-side wireless communication circuit 31 and the display control unit 35 of the diagnostic apparatus main body 3, instead of being disposed inside the B-mode image generation unit 19.

In this case, the B-mode image signal generated by the envelope detection processing in the B-mode signal processing unit 46 of the B-mode image generation unit 19 is wirelessly transmitted from the probe-side wireless communication circuit 20, the B-mode image signal received by the main body-side wireless communication circuit 31 of the diagnostic apparatus main body 3 is subjected to the conversion into the image signal by the DSC 47 and the image processing by the B-mode image processing unit 48, and the B-mode image signal (B-mode image UB) subjected to the image processing is sent to the display control unit 35. The DSC 47 and the B-mode image processing unit 48 disposed in the diagnostic apparatus main body 3 can constitute the main body-side processor 40.

Further, the averaging unit 17 averages the complex baseband signals I and Q at the plurality of sampling points P, but may simply add the complex baseband signals I and Q at the plurality of sampling points P. Even in this case, as compared with the case where the complex baseband signals I and Q immediately after being generated by the detection unit 16 are wirelessly transmitted by the probe-side wireless communication circuit 20, the number of wireless transmissions of the data from the probe-side wireless communication circuit 20 to the diagnostic apparatus main body 3 can be reduced to 1/(number N of sampling points P), and the information amount can be reduced to 1/(number N of sampling points P).

An example has been described in which the sampling point setting unit 26 sets the predetermined number N of sampling points P, but the method of deciding the number N of sampling points P is not limited thereto.

For example, the sampling point setting unit 26 can decide the number N of sampling points P in the Doppler gate DG according to the frequency of the drive signal supplied to each transducer of the transducer array 11 by the transmission circuit 12. Specifically, the sampling point setting unit 26 can set the number N of sampling points such that the number of sampling points P in the Doppler gate DG is increased as the frequency of the drive signal supplied to each transducer of the transducer array 11 by the transmission circuit 12 is increased.

Further, it is preferable that the sampling point setting unit 26 has a lower limit value for the number N of sampling points P decided according to a wirelessly transmittable data amount per unit time based on a wireless connection status between the probe-side wireless communication circuit 20 and the main body-side wireless communication circuit 31. Specifically, the sampling point setting unit 26 can set the number N of plurality of sampling points P in the Doppler gate DG such that a wireless transmission data amount per unit time required for wirelessly transmitting the complex baseband signals I and Q at the plurality of sampling points P without averaging exceeds the wirelessly transmittable data amount and a wireless transmission data amount per unit time required for wirelessly transmitting the average complex baseband signals X and Y is equal to or less than the wirelessly transmittable data amount.

In this case, the probe control unit 22 can acquire information indicating the wireless connection status between the probe-side wireless communication circuit 20 and the main body-side wireless communication circuit 31, from the probe-side wireless communication circuit 20, and can send the acquired information indicating the wireless connection status to the sampling point setting unit 26. Further, for example, the main body control unit 37 can acquire the information indicating the wireless connection status between the probe-side wireless communication circuit 20 and the main body-side wireless communication circuit 31, from the main body-side wireless communication circuit 31, and can wirelessly transmit the acquired information indicating the wireless connection status from the main body-side wireless communication circuit 31 to the ultrasound probe 2. In this case, for example, the information indicating the wireless connection status, which has been wirelessly transmitted from the main body-side wireless communication circuit 31, can be sent to the sampling point setting unit 26 via the probe-side wireless communication circuit 20 and the probe control unit 22.

For example, the complex baseband signals I and Q at the plurality of (N) sampling points P are saved, a gate width of the Doppler gate DG is changed in a state where the Doppler image UD is frozen, and the average complex baseband signals X and Y can be acquired on the basis of the complex baseband signals I and Q at the sampling points P in the Doppler gate DG of which the gate width is changed, among the saved complex baseband signals I and Q at the N sampling points. In this case, the Doppler image generation unit 33 can generate the Doppler image UD on the basis of the average complex baseband signals X and Y corresponding to the Doppler gate DG of which the gate width is changed, and can display the generated Doppler image UD on the monitor 36. Thereby, by using the already generated complex baseband signals I and Q, the Doppler image UD indicating a local blood flow velocity, such as a central portion of the blood vessel with high blood flow velocity, can be obtained, and thus it is possible for the operator to easily perform a more detailed inspection.

Here, the wireless transmission data amount per unit time required for wirelessly transmitting the average complex baseband signals X and Y refer to the information amount of the average complex baseband signals X and Y wirelessly transmitted per unit time, which is required for displaying the Doppler image UD, which is generated by the Doppler image generation unit 33 on the basis of the average complex baseband signals X and Y, in real time on the monitor 36. In this manner, by setting the number N of plurality of sampling points P in the Doppler gate DG, the information amount of the average complex baseband signals X and Y can be reduced in accordance with the wirelessly transmittable data amount per unit time between the probe-side wireless communication circuit 20 and the main body-side wireless communication circuit 31, and thus the Doppler image UD generated by the Doppler image generation unit 33 can be displayed in real time on the monitor 36.

Figure 7:
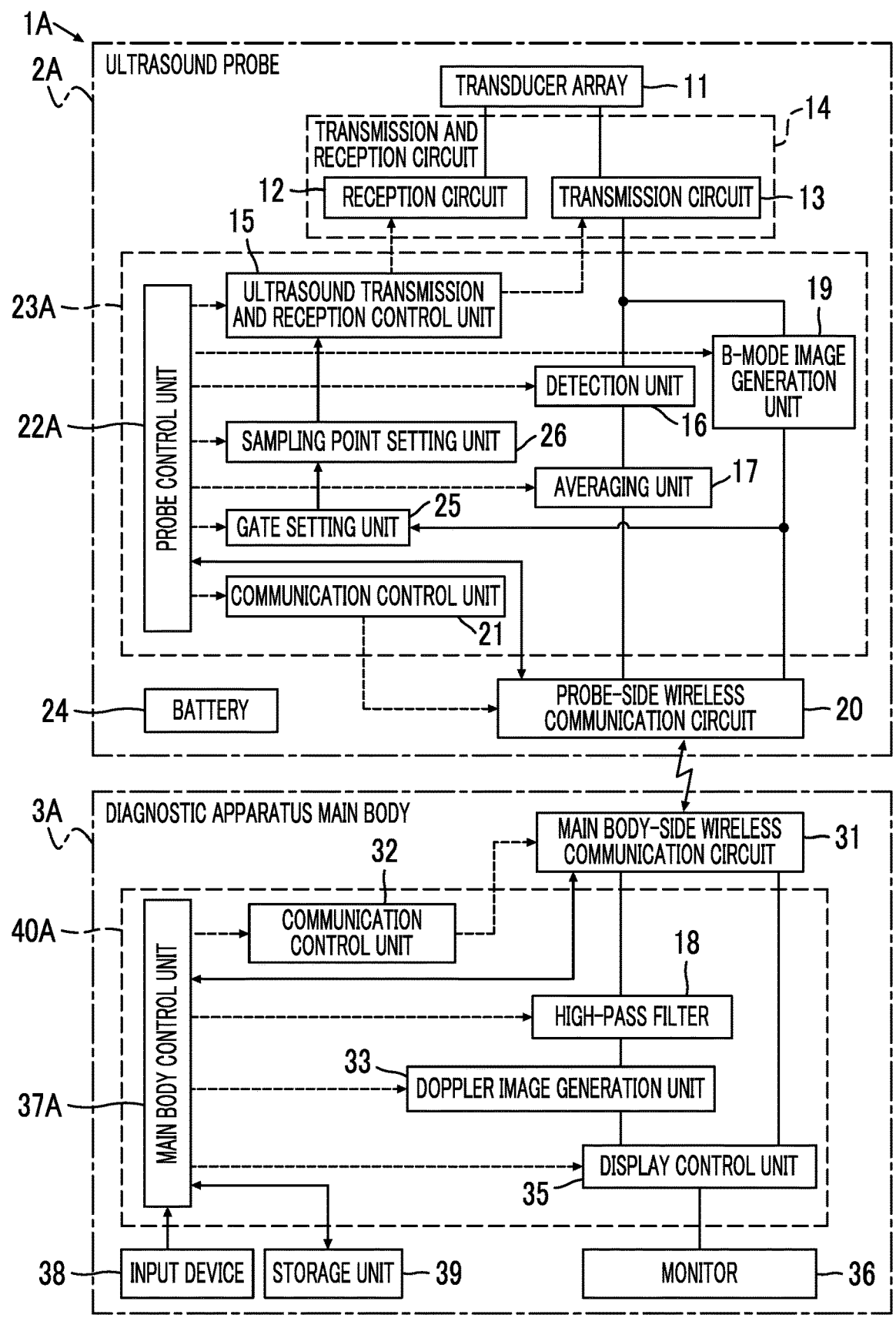
FIG. 7 is a block diagram illustrating a configuration of an ultrasound diagnostic apparatus according to a modification example of the first embodiment of the present invention.

The high-pass filter 18 is provided in the ultrasound probe 2, but may be provided in the diagnostic apparatus main body 3. FIG. 7 illustrates a configuration of an ultrasound diagnostic apparatus 1A according to a modification example of the first embodiment of the present invention. The ultrasound diagnostic apparatus 1A is obtained by comprising an ultrasound probe 2A instead of the ultrasound probe 2 and comprising a diagnostic apparatus main body 3A instead of the diagnostic apparatus main body 3 in the ultrasound diagnostic apparatus 1 of the first embodiment illustrated in FIG. 1. The ultrasound probe 2A is obtained by removing the high-pass filter 18 from the ultrasound probe 2 in the first embodiment, comprising a probe control unit 22A instead of the probe control unit 22, and comprising a probe-side processor 23A instead of the probe-side processor 23. The diagnostic apparatus main body 3A is obtained by adding the high-pass filter 18 to the diagnostic apparatus main body 3 in the first embodiment, comprising a main body control unit 37A instead of the main body control unit 37, and comprising a main body-side processor 40A instead of the main body-side processor 40.

In the ultrasound probe 2A, the probe-side wireless communication circuit 20 is directly connected to the averaging unit 17.

Further, in the diagnostic apparatus main body 3A, the high-pass filter 18 is connected to the main body-side wireless communication circuit 31, and the Doppler image generation unit 33 and the main body control unit 37A are connected to the high-pass filter 18.

In the ultrasound diagnostic apparatus 1A, the average complex baseband signals X and Y acquired by the averaging unit 17 are wirelessly transmitted to the diagnostic apparatus main body 3A by the probe-side wireless communication circuit 20. The main body-side wireless communication circuit 31 receives the average complex baseband signals X and Y wirelessly transmitted from the ultrasound probe 2A, and sends the received average complex baseband signals X and Y to the high-pass filter 18. The high-pass filter 18 performs the high-pass processing on the average complex baseband signals X and Y to remove the clutter signal from the average complex baseband signals X and Y. The Doppler image generation unit 33 generates the Doppler image UD on the basis of the average complex baseband signals X and Y from which the clutter signal is removed by the high-pass filter 18. The Doppler image UD generated in this manner is subjected to the predetermined processing in the display control unit 35, and then is displayed on the monitor 36.

Thus, even in a case where the diagnostic apparatus main body 3A comprises the high-pass filter 18, similarly to the case where the ultrasound probe 2A comprises the high-pass filter 18, it is possible to significantly reduce the information amount of the data wirelessly transmitted from the ultrasound probe 2A to the diagnostic apparatus main body 3A as compared with the case where the complex baseband signals I and Q immediately after being generated by the detection unit 16 are wirelessly transmitted.

Second Embodiment

In the ultrasound diagnostic apparatus 1 of the first embodiment, the Doppler image UD generated by the Doppler image generation unit 33 is displayed on the monitor 36, but a sound corresponding to a graph of the Doppler image UD can be output.

Figure 8:
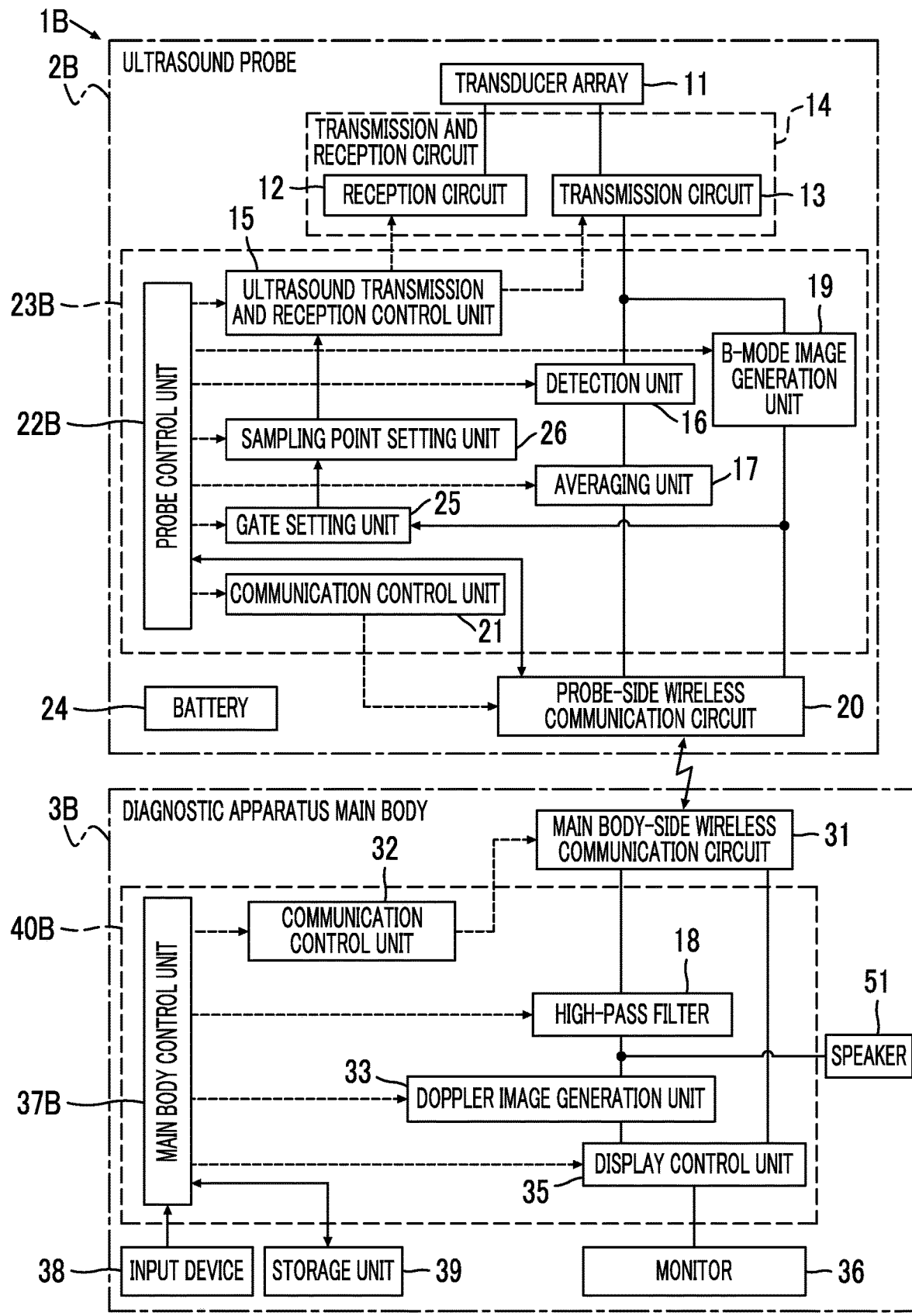
FIG. 8 is a block diagram illustrating a configuration of an ultrasound diagnostic apparatus according to a second embodiment of the present invention.

FIG. 8 illustrates a configuration of an ultrasound diagnostic apparatus 1B according to a second embodiment of the present invention. The ultrasound diagnostic apparatus 1B is obtained by comprising an ultrasound probe 2B instead of the ultrasound probe 2 and comprising a diagnostic apparatus main body 3B instead of the diagnostic apparatus main body 3 in the ultrasound diagnostic apparatus 1 of the first embodiment illustrated in FIG. 1. The ultrasound probe 2B is obtained by removing the high-pass filter 18 from the ultrasound probe 2 in the first embodiment, comprising a probe control unit 22B instead of the probe control unit 22, and comprising a probe-side processor 23B instead of the probe-side processor 23. The diagnostic apparatus main body 3B is obtained by adding the high-pass filter 18 and a speaker 51 to the diagnostic apparatus main body 3 in the first embodiment, comprising a main body control unit 37B instead of the main body control unit 37, and comprising a main body-side processor 40B instead of the main body-side processor 40.

In the ultrasound probe 2B, the probe-side wireless communication circuit 20 is directly connected to the averaging unit 17.

Further, in the diagnostic apparatus main body 3B, the high-pass filter 18 is connected to the main body-side wireless communication circuit 31, and the Doppler image generation unit 33, the main body control unit 37B, and the speaker 51 are connected to the high-pass filter 18.

In the ultrasound diagnostic apparatus 1B, the average complex baseband signals X and Y acquired by the averaging unit 17 are wirelessly transmitted to the diagnostic apparatus main body 3B by the probe-side wireless communication circuit 20. The main body-side wireless communication circuit 31 receives the average complex baseband signals X and Y wirelessly transmitted from the ultrasound probe 2B, and sends the received average complex baseband signals X and Y to the high-pass filter 18. The high-pass filter 18 performs the high-pass processing on the average complex baseband signals X and Y to remove the clutter signal from the average complex baseband signals X and Y. The Doppler image generation unit 33 generates the Doppler image UD on the basis of the average complex baseband signals X and Y from which the clutter signal is removed by the high-pass filter 18. The Doppler image UD generated in this manner is subjected to the predetermined processing in the display control unit 35, and then is displayed on the monitor 36.

Further, the speaker 51 emits a sound on the basis of the average complex baseband signals X and Y from which the clutter signal is removed by the high-pass filter 18. The sound emitted from the speaker 51 is a sound corresponding to the frequency of the waveform of the graph of the Doppler image UD generated by the Doppler image generation unit 33, as illustrated in FIG. 4, for example. Since the clutter signal has been removed from the average complex baseband signals X and Y input to the speaker 51, the sound emitted from the speaker 51 represents a change in blood flow velocity in the blood vessel of the subject, with the influence of the clutter signal removed.

Therefore, with the ultrasound diagnostic apparatus 1B according to the second embodiment of the present invention, it is possible for the operator to intuitively grasp the change in blood flow velocity in the blood vessel of the subject by listening to the sound emitted from the speaker 51.

The high-pass filter 18 in the second embodiment may be the same as or different from the high-pass filter 18 in the first embodiment.

Third Embodiment

In general, in a case where the communication state of the wireless communication is unstable, so-called data loss in which wirelessly transmitted data is lost without being received on the receiving device side may occur, but it is possible to specify and interpolate the data in which the data loss has occurred, by assigning a time stamp to the data to be wirelessly transmitted, for example.

Figure 9:
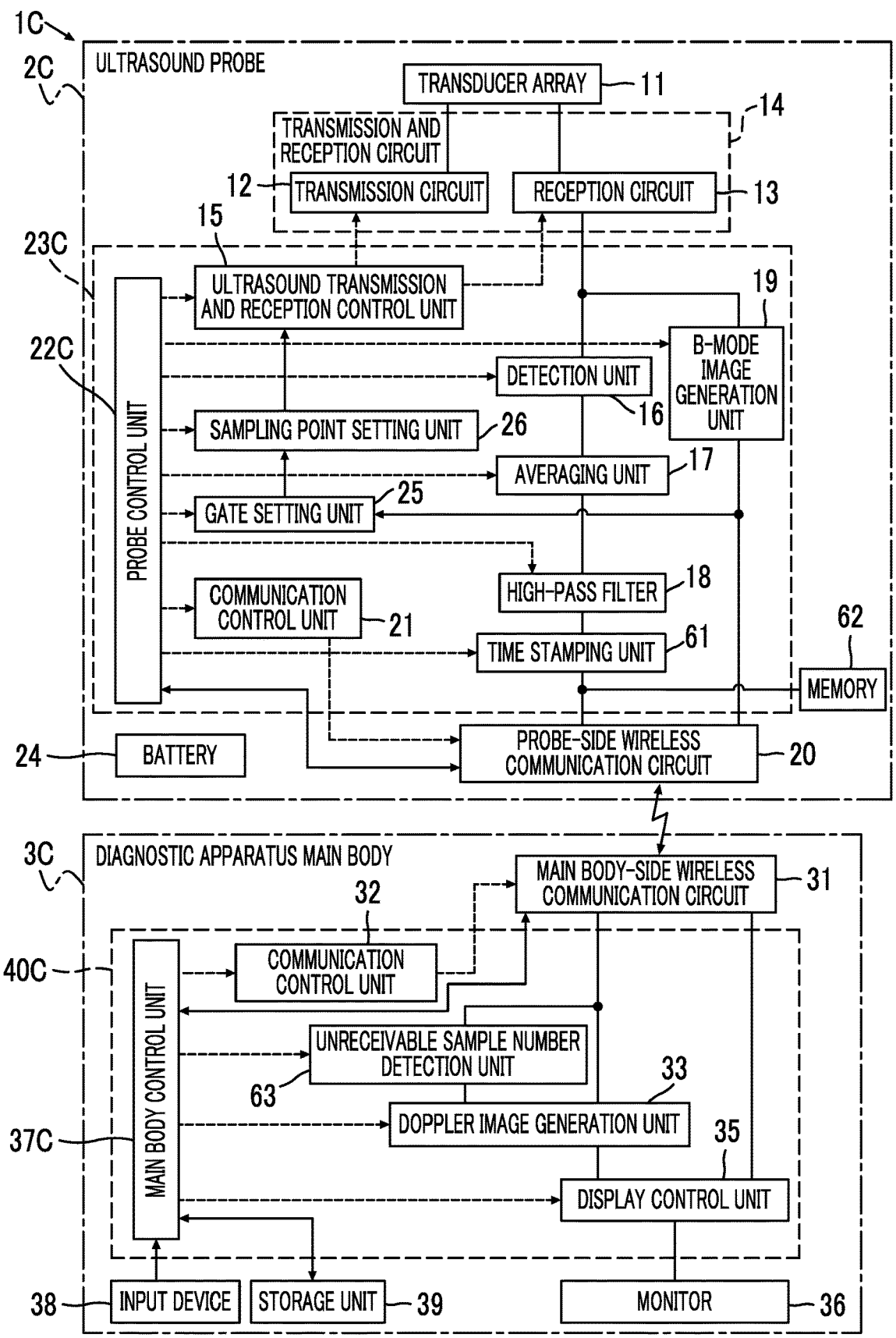
FIG. 9 is a block diagram illustrating a configuration of an ultrasound diagnostic apparatus according to a third embodiment of the present invention.

FIG. 9 illustrates a configuration of an ultrasound diagnostic apparatus 1C according to a third embodiment of the present invention. The ultrasound diagnostic apparatus 1C is obtained by comprising an ultrasound probe 2C instead of the ultrasound probe 2 and comprising a diagnostic apparatus main body 3C instead of the diagnostic apparatus main body 3 in the ultrasound diagnostic apparatus 1 of the first embodiment illustrated in FIG. 1. The ultrasound probe 2C is obtained by adding a time stamping unit 61 and a memory 62 to the ultrasound probe 2 in the first embodiment, comprising a probe control unit 22C instead of the probe control unit 22, and comprising a probe-side processor 23C instead of the probe-side processor 23. The diagnostic apparatus main body 3C is obtained by adding an unreceivable sample number detection unit 63 to the diagnostic apparatus main body 3 in the first embodiment, comprising a main body control unit 37C instead of the main body control unit 37, and comprising a main body-side processor 40C instead of the main body-side processor 40.

In the ultrasound probe 2C, the time stamping unit 61 is connected to the high-pass filter 18, and the probe-side wireless communication circuit 20, the probe control unit 22C, and the memory 62 are connected to the time stamping unit 61.

In the diagnostic apparatus main body 3C, the Doppler image generation unit 33 and the unreceivable sample number detection unit 63 are connected to the main body-side wireless communication circuit 31. Further, the Doppler image generation unit 33 and the main body control unit 37C are connected to the unreceivable sample number detection unit 63.

The time stamping unit 61 assigns a time stamp to the average complex baseband signals X and Y For example, the time stamping unit 61 can assign, as the time stamp, the time when the average complex baseband signals X and Y are acquired by the averaging unit 17, to the average complex baseband signals X and Y. Further, for example, the time stamping unit 61 can assign, as the time stamp, a serial number indicating the order in which the average complex baseband signals X and Y are acquired by the averaging unit 17, to the average complex baseband signals X and Y.

The memory 62 saves the average complex baseband signals X and Y to which the time stamp is assigned by the time stamping unit 61. The average complex baseband signals X and Y are obtained by averaging the complex baseband signals I and Q at the plurality of sampling points P in the Doppler gate DG, and have a smaller information amount than that of the complex baseband signals I and Q. Therefore, the average complex baseband signals X and Y with a larger number of pieces of data can be saved in the memory 62 as compared with the case when the complex baseband signals I and Q are saved in the memory 62.

The unreceivable sample number detection unit 63 detects the number of samples of the average complex baseband signals X and Y that could not be consecutively received in time series by the main body-side wireless communication circuit 31, on the basis of the time stamp assigned to the average complex baseband signals X and Y.

In a case where the number of samples detected by the unreceivable sample number detection unit 63 is one to a sample number threshold value, the Doppler image generation unit 33 can perform interpolation processing on the average complex baseband signals X and Y in which the data loss has occurred, on the basis of the values of the plurality of average complex baseband signals X and Y received by the main body-side wireless communication circuit 31. In this case, for example, the Doppler image generation unit 33 can interpolate the velocity values corresponding to the average complex baseband signals X and Y in which the data loss has occurred, to generate the Doppler image UD. In this case, for example, the Doppler image generation unit 33 can estimate the waveform of the graph in the Doppler image UD as an approximation curve on the basis of the values of the plurality of average complex baseband signals X and Y received by the main body-side wireless communication circuit 31, and can interpolate the velocity values corresponding to the average complex baseband signals X and Y in which the data loss has occurred, on the basis of the estimated approximation curve. Further, the Doppler image generation unit 33 can also interpolate a portion where the waveform of the graph is missing in the Doppler image UD, which is generated on the basis of the values of the plurality of average complex baseband signals X and Y received by the main body-side wireless communication circuit 31, with a straight line.

In a case where the number of samples detected by the unreceivable sample number detection unit 63 exceeds the sample number threshold value, the Doppler image generation unit 33 determines that the data cannot be interpolated, stop the generation of the Doppler image UD, and display an image filled in black instead of the Doppler image UD.

For example, in a case where the average complex baseband signals X and Y in which the data loss has occurred are detected by the unreceivable sample number detection unit 63 and the display of the Doppler image UD on the monitor 36 by the Doppler image generation unit 33 is frozen, the probe-side wireless communication circuit 20 can wirelessly transmit the average complex baseband signals X and Y saved in the memory 62 to the diagnostic apparatus main body 3C. In this case, the Doppler image generation unit 33 can perform a frequency analysis on the average complex baseband signals X and Y that have been saved in the memory 62, instead of the lost average complex baseband signals X and Y, on the basis of the time stamp assigned to the average complex baseband signals X and Y, to generate again the Doppler image UD, and can display the newly generated Doppler image UD on the monitor 36.

From the above, with the ultrasound diagnostic apparatus 1C according to the third embodiment of the present invention, even in a case where data loss occurs in the average complex baseband signals X and Y wirelessly transmitted from the probe-side wireless communication circuit 20, the average complex baseband signals X and Y in which the data loss has occurred can be specified by the time stamp assigned to the average complex baseband signals X and Y, and the interpolation of the average complex baseband signals X and Y or the re-generation of the Doppler image UD on the basis of the average complex baseband signals X and Y saved in the memory 62 is performed. Therefore, it is possible for the operator to accurately grasp the Doppler image UD.

Further, the average complex baseband signals X and Y are obtained by averaging the complex baseband signals I and Q at the plurality of sampling points P in the Doppler gate DG, and have a smaller information amount than that of the complex baseband signals I and Q. Therefore, the average complex baseband signals X and Y with a larger number of pieces of data can be saved in the memory 62 as compared with the case when the complex baseband signals I and Q are saved in the memory 62. Therefore, the Doppler image generation unit 33 can generate again the Doppler image UD corresponding to more average complex baseband signals X and Y on the basis of the average complex baseband signals X and Y saved in the memory 62.

EXPLANATION OF REFERENCES 1, 1A, 1B, 1C: ultrasound diagnostic apparatus
2, 2A, 2B, 2C: ultrasound probe
3, 3A, 3B, 3C: diagnostic apparatus main body
11: transducer array
12: transmission circuit
13: reception circuit
14: transmission and reception circuit
15: ultrasound transmission and reception control unit
16: detection unit
17: averaging unit
18: high-pass filter
19: B-mode image generation unit
20: probe-side wireless communication circuit
21, 32: communication control unit
22, 22A, 22B, 22C: probe control unit
23, 23A, 23B, 23C: probe-side processor
24: battery
25: gate setting unit
26: sampling point setting unit
31: main body-side wireless communication circuit
33: Doppler image generation unit
35: display control unit
36: monitor
37, 37A, 37B, 37C: main body control unit
38: input device
39: storage unit
40, 40A, 40B, 40C: main body-side processor
41: amplification unit
42: AD conversion unit
43: beam former
44: high-pass filter
45: autocorrelation unit
46: B-mode signal processing unit
47: DSC
48: B-mode image processing unit
51: speaker
61: time stamping unit
62: memory
63: unreceivable sample number detection unit
B1: blood vessel region
DG: Doppler gate
N: number
P: sampling point
SL: straight line portion
UB: B-mode image
UD: Doppler image

What is claimed is:
1. An ultrasound diagnostic apparatus comprising:
an ultrasound probe including a transducer array and a diagnostic apparatus main body including a monitor, where the ultrasound probe and the diagnostic appara- tus main body are wirelessly connected to each other; and a B-mode and a pulsed wave Doppler mode, wherein the ultrasound probe includes
- a transmission and reception circuit configured to
  - cause the transducer array to transmit an ultrasonic pulse toward a subject, and
  - perform reception focusing processing on a reception signal output from the transducer array that has received an ultrasound echo from the subject to generate a sound ray signal,
- a first processor configured to
  - generate a B-mode image based on the sound ray signal generated by the transmission and reception circuit,
  - set a Doppler gate on the B-mode image,
  - set a number of a plurality of sampling points within the Doppler gate on the B-mode image,
  - generate complex baseband signals at the plurality of sampling points based on the sound ray signal generated by the transmission and reception circuit,
  - average the complex baseband signals at the plurality of sampling points to acquire average complex baseband signals,
- where a number of the plurality of sampling points in the Doppler gate is set such that a wireless transmission data amount per unit time required for wirelessly transmitting the complex baseband signals at the plurality of sampling points without averaging exceeds the wirelessly transmittable data amount and a wireless transmission data amount per unit time required for wirelessly transmitting the average complex baseband signals is equal to or less than the wirelessly transmittable data amount, and
- a probe-side wireless communication circuit configured to wirelessly transmit the average complex baseband signals acquired by the first processor, and the diagnostic apparatus main body includes
- a main body-side wireless communication circuit configured to receive the average complex baseband signals wirelessly transmitted from the probe-side wireless communication circuit, and
- a second processor configured to
  - perform a frequency analysis on the average complex baseband signals received by the main body-side wireless communication circuit to generate a Doppler image, and
  - display the Doppler image on the monitor.

2. The ultrasound diagnostic apparatus according to claim 1,
wherein the first processor is further configured to perform high-pass processing on the average complex baseband signals, and
the probe-side wireless communication circuit is further configured to wirelessly transmit the average complex baseband signals that are subjected to the high-pass processing by a high-pass filter.

3. The ultrasound diagnostic apparatus according to claim 1,
wherein the second processor is further configured to perform high-pass processing on the average complex baseband signals received by the main body-side wireless communication circuit, and
perform the frequency analysis on the average complex baseband signals that are subjected to the high-pass processing.

4. The ultrasound diagnostic apparatus according to claim 1,
wherein the second processor is further configured to perform the frequency analysis on the average complex baseband signals received by the main body-side wireless communication circuit by performing a fast Fourier transform.

5. The ultrasound diagnostic apparatus according to claim 1,
wherein the first processor is further configured to assign a time stamp to the average complex baseband signals.

6. The ultrasound diagnostic apparatus according to claim 3,
wherein the diagnostic apparatus main body includes a speaker, wherein the average complex baseband signals that are subjected to the high-pass processing are input into the speaker.

7. The ultrasound diagnostic apparatus according to claim 5,
wherein the second processor is further configured to detect the number of samples of the average complex baseband signals that could not be received by the main body-side wireless communication circuit, based on the time stamp assigned to the average complex baseband signals.

8. The ultrasound diagnostic apparatus according to claim 7,
wherein when the number of samples is equal to or less than a predetermined threshold value,
the second processor is further configured to
perform interpolation processing on the average complex baseband signals, and
generate the Doppler image based on the average complex baseband signals which is interpolated.

9. The ultrasound diagnostic apparatus according to claim 7,
wherein the second processor is further configured to stop the generation of the Doppler image when the number of samples exceeds a threshold value.

10. The ultrasound diagnostic apparatus according to claim 7,
wherein the ultrasound probe includes a memory that saves the average complex baseband signals,
the probe-side wireless communication circuit wirelessly transmits the average complex baseband signals saved in the memory to the diagnostic apparatus main body when the display of the Doppler image on the monitor by the second processor is frozen, and
the second processor is further configured to
perform the frequency analysis on the average complex baseband signals that have been saved in the memory, instead of a lost average complex baseband signals, based on the time stamp assigned to the average complex baseband signals, to generate again the Doppler image, and
display the Doppler image on the monitor.

11. A control method of an ultrasound diagnostic apparatus that includes an ultrasound probe including a transducer array and a diagnostic apparatus main body including a monitor, where the ultrasound probe and the diagnostic apparatus main body are wirelessly connected to each other; and a B-mode and a pulsed wave Doppler mode, the control method comprising:
in the ultrasound probe,
causing, via a transmitting and receiving circuit of the ultrasound probe, the transducer array to transmit an ultrasonic pulse toward a subject, and performing reception focusing processing on a reception signal output from the transducer array that has received an ultrasound echo from the subject to generate a sound ray signal, generating, via a first processor of the ultrasound probe, a B-mode image based on the generated sound ray signal, setting, via the first processor, a Doppler gate on the B-mode image, setting, via the first processor, a number of a plurality of sampling points within the Doppler gate on the B-mode image, generating, via the first processor, complex baseband signals at the plurality of sampling points based on the generated sound ray signal, averaging, via the first processor, the complex the complex baseband signals at the plurality of sampling points to acquire average complex baseband signals, and wirelessly transmitting, via a probe-side wireless communication circuit of the ultrasound probe, the acquired average complex baseband signals, where a number of the plurality of sampling points in the Doppler gate is set such that a wireless transmission data amount per unit time required for wirelessly transmitting the complex baseband signals at the plurality of sampling points without averaging exceeds the wirelessly transmittable data amount and a wireless transmission data amount per unit time required for wirelessly transmitting the average complex baseband signals is equal to or less than the wirelessly transmittable data amount, and in the diagnostic apparatus main body, receiving, via a main body-side wireless communication circuit of the diagnostic apparatus body, the average complex baseband signals wirelessly transmitted from the ultrasound probe, and performing, via a second processor of the diagnostic apparatus, a frequency analysis on the received average complex baseband signals to generate a Doppler image, and displaying the Doppler image on the monitor.

* * * * *